United States Patent [19]
Vo-Dinh

[11] Patent Number: 5,864,397
[45] Date of Patent: Jan. 26, 1999

[54] SURFACE-ENHANCED RAMAN MEDICAL PROBES AND SYSTEM FOR DISEASE DIAGNOSIS AND DRUG TESTING

[75] Inventor: Tuan Vo-Dinh, Knoxville, Tenn.

[73] Assignee: Lockheed Martin Energy Research Corporation, Oak Ridge, Tenn.

[21] Appl. No.: 929,612

[22] Filed: Sep. 15, 1997

[51] Int. Cl.[6] .................................................. G01J 3/44
[52] U.S. Cl. .............................................................. 356/301
[58] Field of Search .................................... 356/301, 300; 600/310, 314, 315, 316, 317, 318, 322, 323

[56] References Cited

U.S. PATENT DOCUMENTS

| | | |
|---|---|---|
| 4,781,458 | 11/1988 | Angel et al. . |
| 4,802,761 | 2/1989 | Bowen et al. . |
| 4,917,491 | 4/1990 | Ring et al. . |
| 5,017,007 | 5/1991 | Milne et al. . |
| 5,112,127 | 5/1992 | Carrabba et al. . |
| 5,261,410 | 11/1993 | Alfano et al. . |
| 5,293,438 | 3/1994 | Konno et al. . |
| 5,400,136 | 3/1995 | Vo-Dinh . |
| 5,404,218 | 4/1995 | Nave et al. . |

*Primary Examiner*—K. P. Hantis
*Attorney, Agent, or Firm*—Quarles & Brady LLP

[57] ABSTRACT

A probe for a surface-enhanced Raman scattering spectrometer includes a member of optically transmissive material for receiving the excitation radiation from a laser and for carrying the radiation emitted from a specimen to a detector. An end of the member for placing against the specimen has a coating that produces surface enhancement of the specimen during Raman scattering spectroscopic analysis. Specifically the coating is formed by a first layer of microparticles on the member and a metal layer over the first layer. The first layer may form a microstructure surface over which a metal layer is applied. Alternatively the coating may be a material containing microparticles of a metal. An optional layer of a material may be applied to the metal layer to concentrate onto the probe compounds of analytical interest onto the probe.

18 Claims, 17 Drawing Sheets

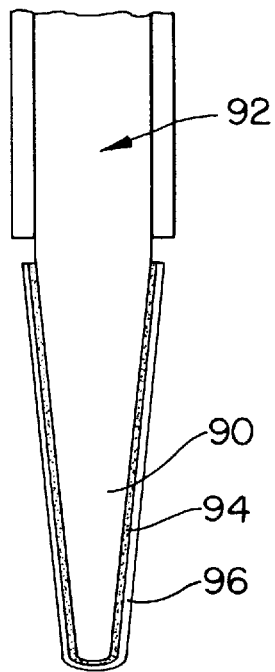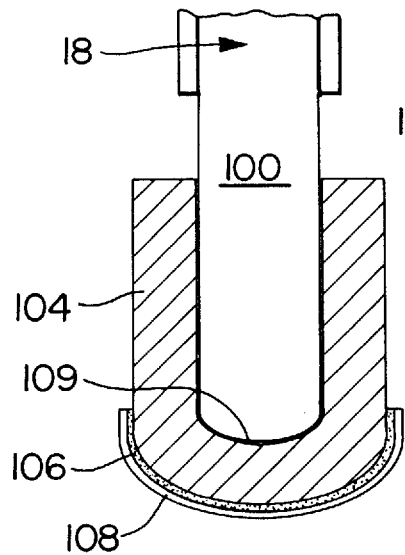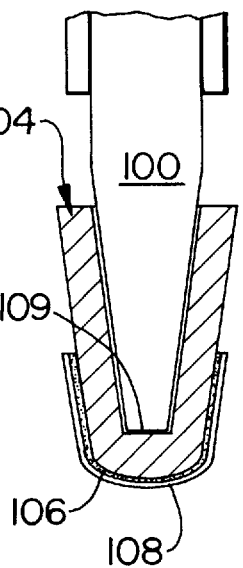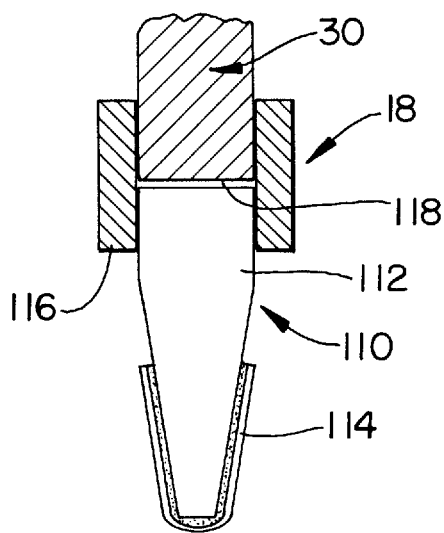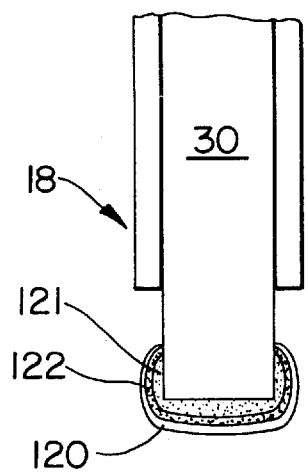

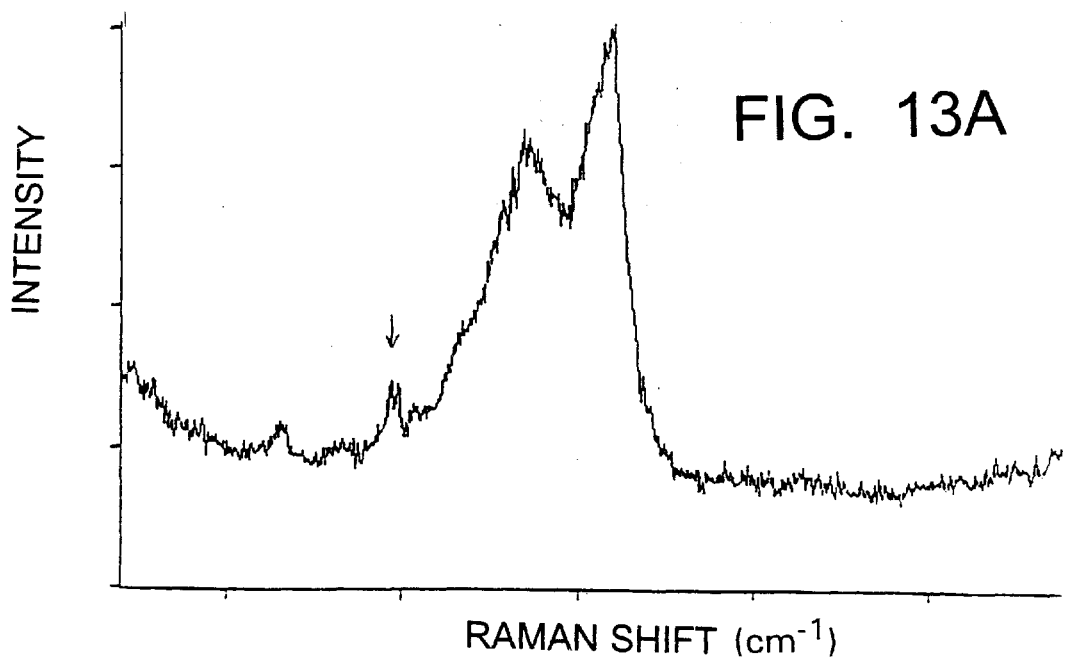
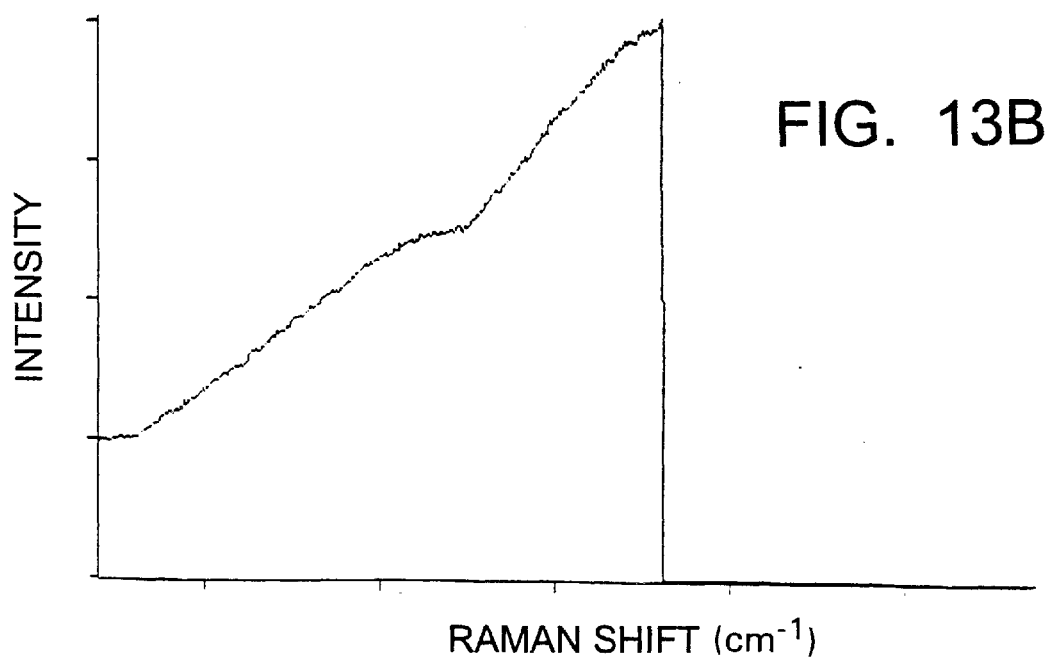

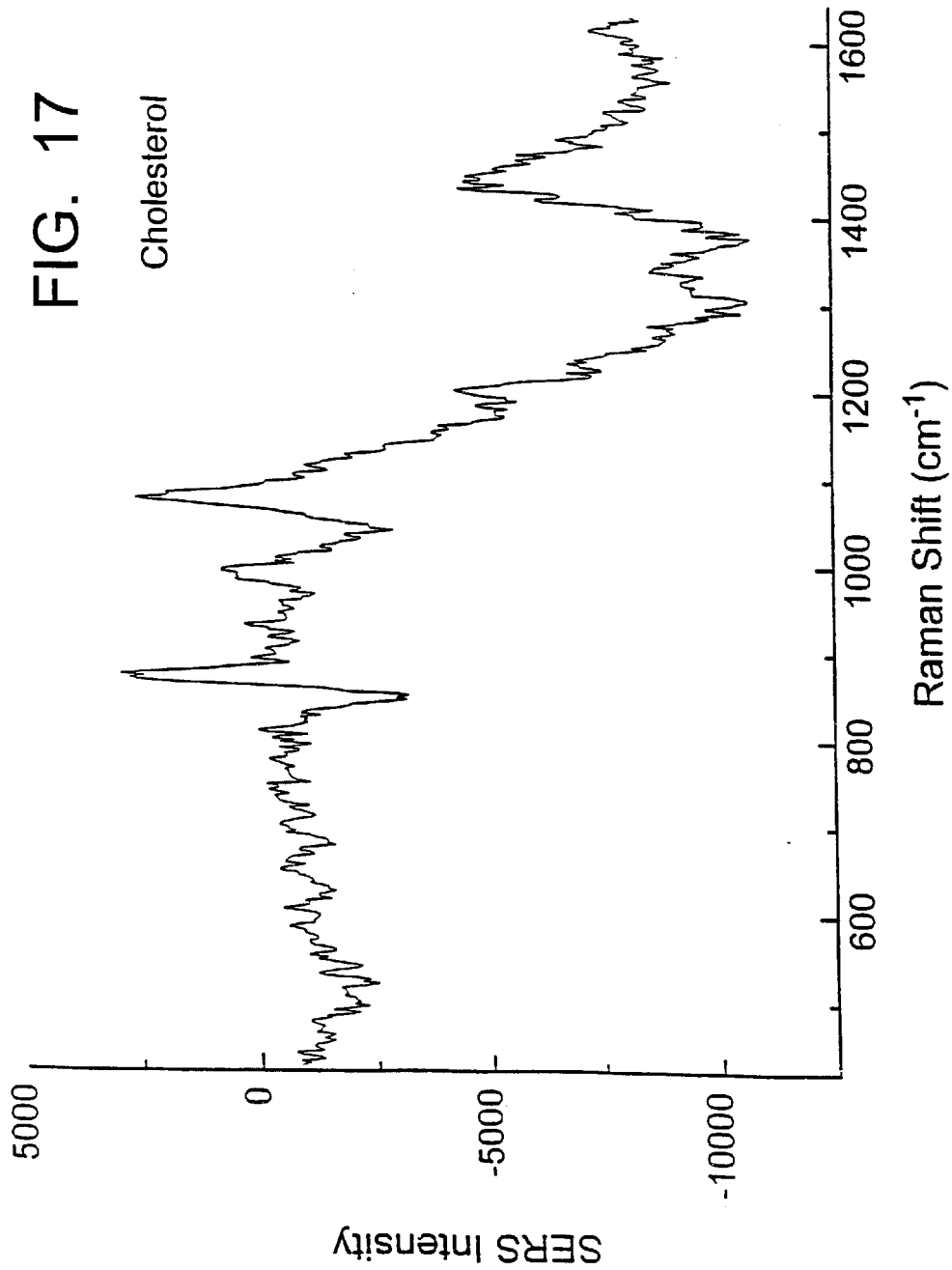

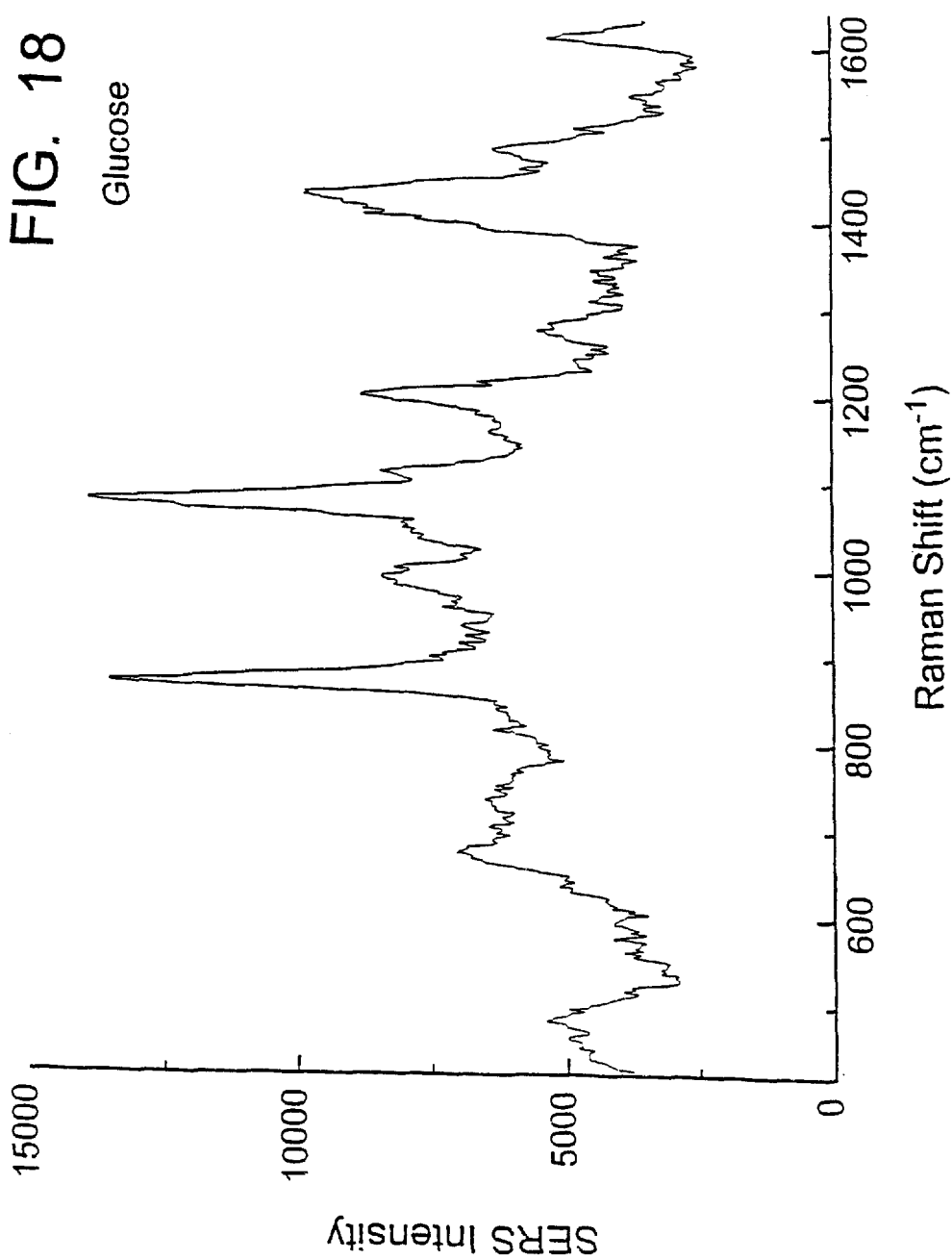

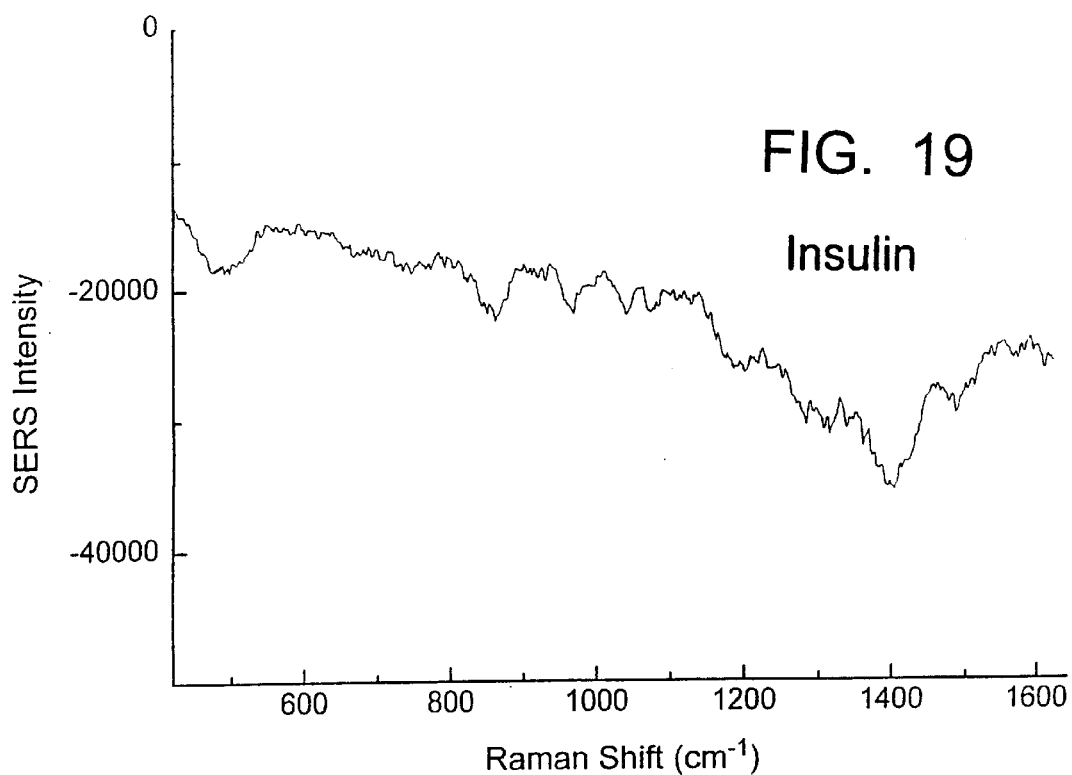
FIG. 19 Insulin
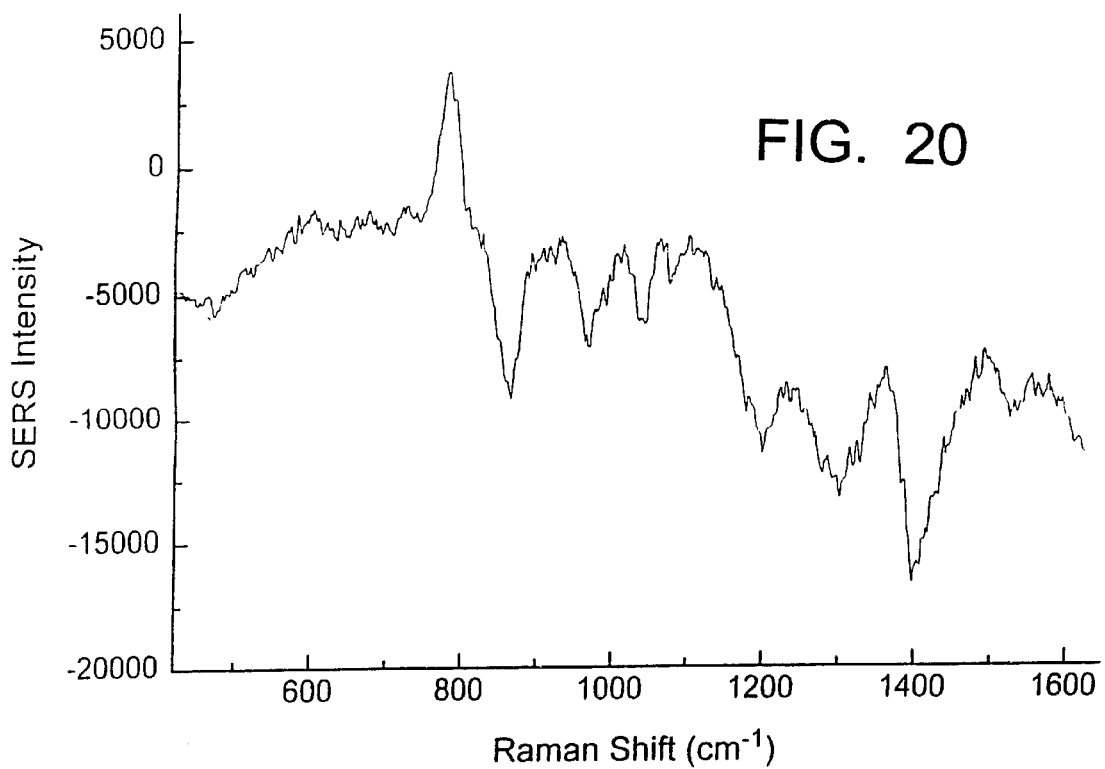
FIG. 20

L-Lactic Acid

SURFACE-ENHANCED RAMAN MEDICAL PROBES AND SYSTEM FOR DISEASE DIAGNOSIS AND DRUG TESTING

This invention was made with government support under contract DE-AC05-96OR22464 awarded by the U.S. Department of Energy to Lockheed Martin Energy Research Corporation, and the United States Government has certain rights in this invention.

BACKGROUND OF THE INVENTION

The present invention relates to apparatus and methods for non-invasive techniques to detect diseases and for drug testing, to Raman spectroscopy and surface enhanced Raman spectroscopy.

Normal Raman spectroscopy relates to the scattering of light from a gas, liquid or solid with a shift in wavelength from that of the usually monochromatic incident radiation. Upon irradiation of a molecule with light in biological applications, the incident radiation having a frequency $v$ should produce scattered radiation, the most intense part of which has unchanged frequency. In addition, if the polarization of a molecule changes as it rotates or vibrates, there are spectral lines of much lesser intensity at frequencies $v \pm v_k$, where $v_k$ is the molecular frequency of rotation or vibration.

Laser-induced fluorescence techniques have been used for cancer diagnosis. Normal Raman spectroscopy (NRS) also has been suggested as an alternate biomedical diagnostic tool since the Raman signals can provide complementary spectral information. However, Raman spectroscopy has several limitations. Intensity of the Raman signal is intrinsically weak and interference from the fluorescence signal is a major problem for the weak signals. In addition weak Raman signals often require sophisticated Fourier transform processing which requires relatively expensive equipment. The requirement of high-power lasers, present potential hazards for in vivo measurements, even with Fourier transform processing.

Fleischmann et al. first reported strongly enhanced Raman scattering from pyridine molecules adsorbed on silver electrode surfaces that had been roughened electrochemically by oxidation-reduction cycles (Chem. Phys. Lett. 26, 163, 1974). This increase in Raman signal, originally attributed to a high surface density produced by the roughening of the surface of electrodes, was later identified by Jeanmaire and Van Duyne (J. Electroanal. Chem. 84, 1, 1977) and independently by Albrecht and Creighton (J. Am. Chem. Soc. 99, 5215, 1977) as a direct result of a surface enhancement process, hence the term surface-enhanced Raman scattering (SERS) effect. In spite of extensive basic research in the 1970's, SERS started to become a useful and practical analytical technique only in the mid-1980's. Vo-Dinh and coworkers first reported the general applicability of SERS as an analytical technique for a variety of chemicals including several homocyclic and heterocyclic polyaromatic compounds on cellulose-based substrates covered with silver-coated microspheres, (T. Vo-Dinh, *Surface-Enhanced Raman Spectroscopy, in Chemical Analysis of Polycyclic Aromatic Compounds,* Wiley, New York, 1989; and T. Vo-Dinh, *Surface-Enhanced Raman Spectroscopy, in Photonic Probes of Surfaces,* Elsevier, New York, 1995). The origin of the enormous Raman enhancement appears to come from the results of several electromagnetic and chemical mechanisms. The observed Raman scattering signals for the adsorbed molecules were found to be more than a million times larger than those expected from gas phase molecules or from non-adsorbed compounds. These enormous enhancement factors, which help compensate for the normally weak Raman scattering process, open new horizons to the Raman technique.

Surface-enhanced Raman scattering (SERS) techniques enhance the Raman signal up to $10^8$ fold. Extensive efforts have been devoted to determining and investigating sources of that enhancement. There are at least two major types of mechanisms that contribute to the SERS effect: a) an electromagnetic effect associated with large local fields caused by electromagnetic resonances occurring near metal surface structures, and b) a chemical effect involving a scattering process associated with chemical interactions between the molecule ans the metal surface.

Although SERS techniques have been used for biochemical analysis, there has been no previous works on SERS-based techniques and instrument for in situ and in vivo biomedical diagnosis and drug testing. Perhaps this is because there are several problems associated with the use of SERS in biomedical applications. Until now, the SERS approaches, which use electrode systems or silver sol media, involve only in vitro samples and do not allow in vivo analysis.

SUMMARY OF THE INVENTION

A general object of the present invention is to provide a surface-enhanced Raman medical (SERMED) diagnostic instrument and method, which increases the Raman emission of tissues due to the surface-enhanced Raman scattering effect.

Another object is to provide a SERMED diagnostic instrument for in situ and in vivo analysis.

A further object of the present invention is to provide a SERMED diagnostic instrument which decreases interference due to the electromagnetic damping effect and does not require high-power excitation lasers.

These and other objectives are satisfied by a probe for a surface-enhanced Raman scattering spectrometer which includes a member of optically transmissive material for receiving the excitation radiation from a source and for carrying the radiation emitted from a specimen to a detector. An end of the probe for placing against the specimen has a coating that produces surface enhancement of the specimen during Raman scattering spectroscopic analysis. Specifically the coating is formed by a first layer of microparticles on the member and a metal layer over the first layer. Preferably, the first layer is formed by particles of alumina, while the second layer may be formed of silver, gold, nickel, copper or cadmium. An optional layer of a material may be applied to the metal layer to concentrate onto the probe compounds of analytical interest onto the probe.

In another embodiment, the probe comprises material having a microstructured surface with a metal layer thereon. Yet another embodiment provides a probe formed of a material with embedded metal nano-particles. In any of the aforementioned embodiments, an optional layer of a material may be applied to the metal layer or material with embedded metal nano-particles to concentrate onto the probe compounds of analytical interest onto the probe.

The present probe for a SERMED diagnostic instrument has particular suitability for in situ and in vivo analysis for disease diagnosis and drug testing as describe subsequently.

BRIEF DESCRIPTION OF THE DRAWINGS

FIG. 5 illustrates a second embodiment of a probe for the SERMED apparatus;

FIGS. 6A–6B illustrate two versions of a third embodiment of a probe for the SERMED apparatus;

FIG. 7 illustrates a fourth embodiment of a probe for the SERMED apparatus;

FIG. 8 illustrates a fifth embodiment of a probe for the SERMED apparatus;

FIGS. 13A and 13B show the SERS spectrum and NRS spectrum respectively of a homogenized sample of rat heart tissue;

FIG. 17 illustrates the results of SERMED analysis to identify and quantify cholesterol;

FIG. 18 illustrates SERMED analysis results to identify and quantify glucose for diagnosis and treatment of diabetes;

FIG. 19 shows results of SERMED analysis to identify and quantify insulin for monitoring diabetics;

FIG. 20 graphically depicts the results of SERMED analysis to identify and quantify NADH;

DETAILED DESCRIPTION OF THE INVENTION

Figure 1A:
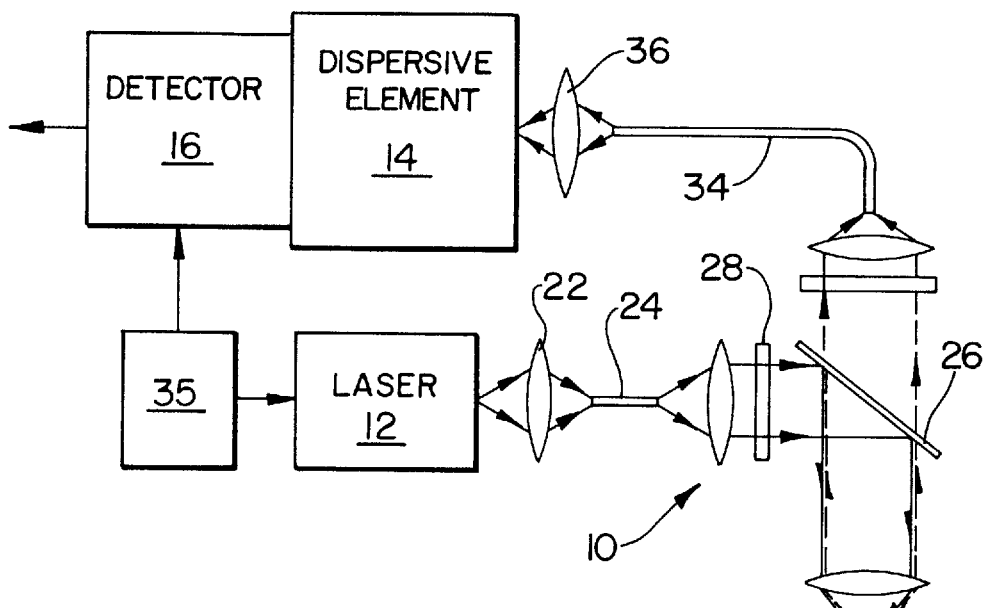
FIG. 1A is a block diagram of a surface-enhanced Raman scattering (SERS) instrument for medical applications.

With reference to FIG. 1A, the basic components of a surface-enhanced Raman scattering medical (SERMED) instrument 10 comprise a monochromatic excitation source 12, a dispersive element 14, a photometric detector 16 and a probe 18. Since the SERS signal is much stronger than the NRS signal and often at a higher frequency than the laser-scattered stray light, the monochromators and related optical instrumentation for SERMED do not need to be sophisticated and costly.

SERMED Instruments

The excitation light source 12 is a laser, such as a argon ion laser with 514 nm excitation, or a krypton ion laser with 647 nm excitation. However helium neon, diode and other types of lasers also can be used with other excitation wavelengths. Laser excitation sources may be selected by the frequencies that can be matched to the surface plasmon resonance frequencies and/or electronic absorption of the compound of interest (resonance Raman effect) in order to take advantage of maximum enhancement. Light from one or several lasers may be used in a multi-photon excitation mode to irradiate the sample. The SERS emission from the sample is collected using a SERMED probe, transmitted through appropriate optics and focused onto the entrance slit of a dispersive element The output of the laser 12 is coupled by a lens 22 to an input optical fiber 24 that leads to the input of a beam splitter 26. The laser radiation is passed through an optical bandpass filter 28 to reject unwanted plasma lines before passing through the beam splitter. The radiation from the laser exiting the beam splitter enters one end of a probe optical fiber 30 which has another end connected to probe 18.

The probe 18 directs the laser radiation toward the biological specimen 32 being examined and receives return radiation that has been reflected and scatted by that specimen. The return radiation travels from the probe 18 through the probe optical fiber 30 and beam splitter 26 into a detector optical fiber 34. The detector optical fiber 34 is coupled by a lens 36 to the input of the dispersive element 14 that has an output connected to the photometric detector 16. The SERMED diagnostic instrument 10 may be a single channel instrument in that all of the return radiation is focused onto a single detector element or it may be a multi-channel instrument. With reference to FIG. 1A, the single channel instrument uses a monochromator as the dispersive element 14 and a photomultiplier as the detector 16. A multi-channel detector, such as a charge coupled device (CCD), or a photodiode array (PDA) equipped with a polychromator can also be employed to record and analyze the Raman spectrum. A photomultiplier equipped with an acousto-optic tunable filter or a liquid crystal tunable filter (LCTF) also can be employed to select and analyze the Raman emission from the specimen 32.

Figure 1B:
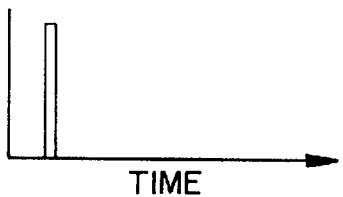
FIGS. 1B–1D graphically depict the timing of several events during the operation of the SERS instrument using a time-resolved method.
Figure 1C:
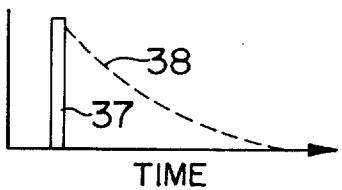
Figure 1D:
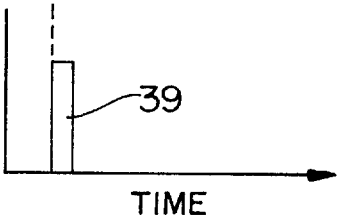

The basic SERMED diagnostic instrument 10 shown in FIG. 1A can be modified to provide time-resolved detection. This variation employs a pulsed laser and a gated detector 16 both of which are controlled by a synchronizer. The synchronizer 38 issues a control signal to the laser 16 which responds by emitting a radiation pulse as shown graphically in FIG. 1B. This excites the specimen 32 to produce a Raman response 37 and fluorescence response 38 as depicted in FIG. 1C. At the same time, the synchronizer 38 issues a control signal which enables the detector 16 for a period of time 39 that forms a detection window as illustrated in FIG. 1D. In this embodiment, the analysis time is synchronized with the laser excitation because the Raman scattering process is very fast, instantaneous with respect to laser excitation. The slower (nanosecond) fluorescence emission of the sample can be therefore discriminated, i.e. gated out.

Figure 2:
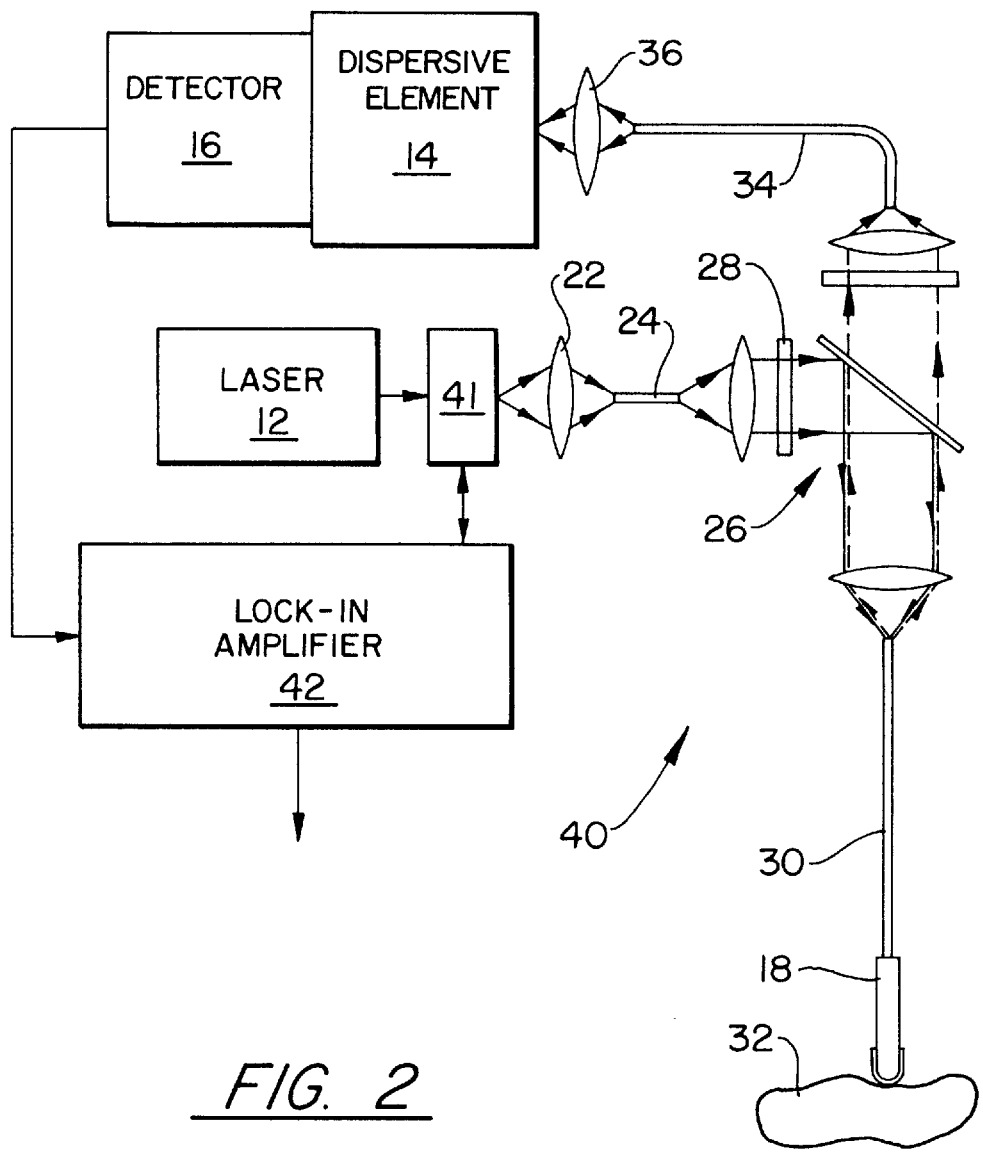
FIG. 2 is a block diagram of a second embodiment of a SERS instrument using a phase-resolved method.

Another discrimination technique, referred to as phase resolution, is employed by the SERMED instrument shown in FIG. 2. This phase-resolved SERMED device 40 is equipped with an intensity modulated laser source, such as by placing an electro-optic modulator 41 between laser 12 and the lens 22 at the input to the input optical fiber 24. A detector 16 also is incorporated. Both the modulator 41 and the detector 16 are controlled by a lock-in amplifier 42. In this embodiment, mode-lock detection allows discrimination against fluorescence, thus improving the detection of the SERS signal.

Figure 3:
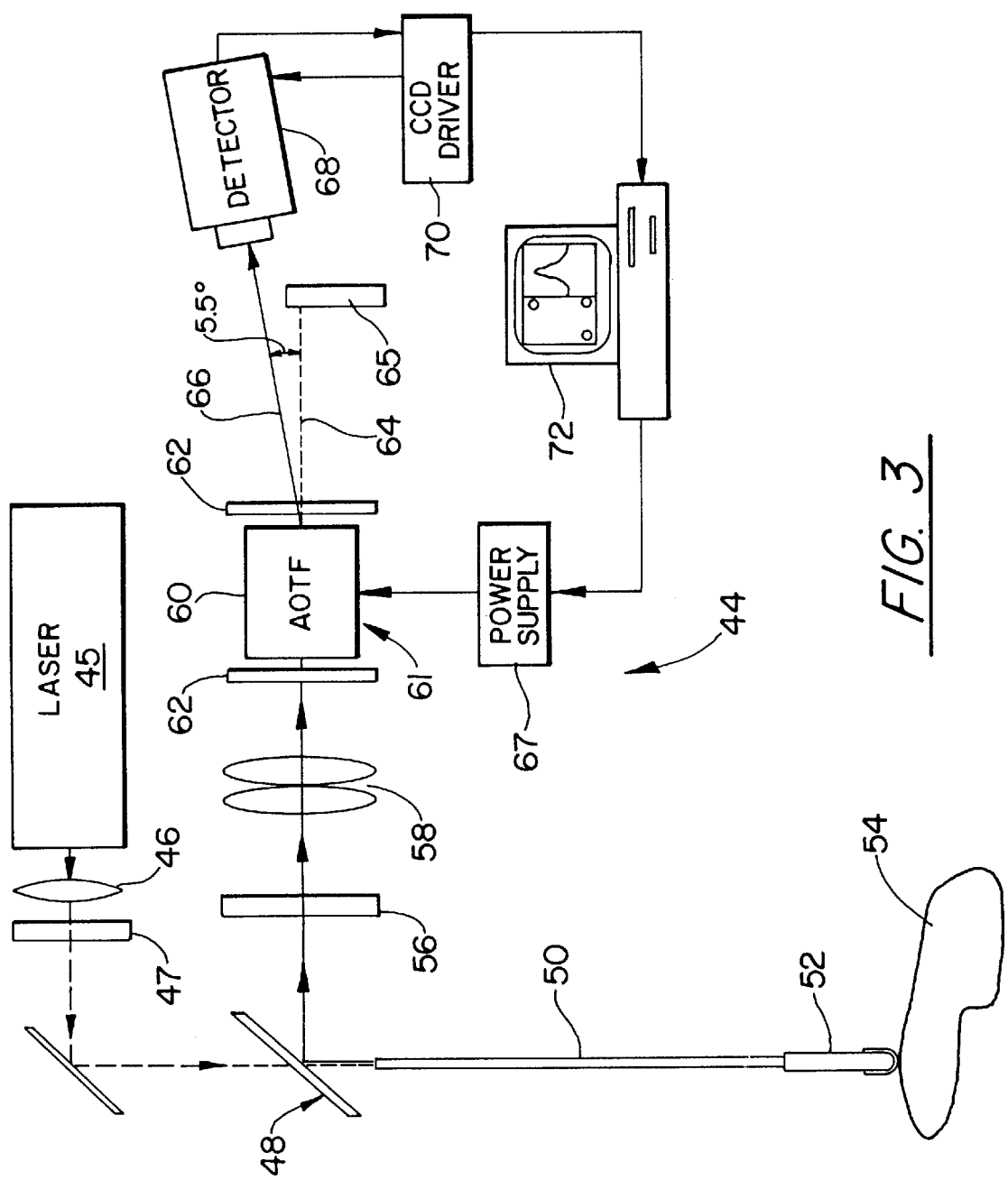
FIG. 3 is a block diagram of a third embodiment of a spectral imaging SERS instrument.

A multi-channel, surface-enhanced Raman scattering instrument 44 shown in FIG. 3 acquires an two dimensional array of Raman spectra, which in addition to being processed as in the single channel version, also produce a Raman image of the specimen being examined. This configuration, referred to as a spectral imaging SERMED instrument, uses an AOTF 61 interfaced to a multi-channel detector 68, such as a vidicon, a photodiode array, a charge coupled device (CCD) or charge injection device (CID).

In the spectral imaging SERMED instrument 40, the radiation from laser 45 passes through a lens 46, a bandpass filter 47 and then into a beam splitter 48. The radiation then travels to a probe 52 through an optical cable 50 that comprises a bundle of optical fibers in a two-dimensional matrix. The radiation from the specimen 54 being examined travels back through the probe 52 and optical cable 50 to the beam splitter 48. The return radiation exits beam splitter 48 and passes through a holographic notch filter 56 and imaging lenses 58. An acousto-optic tunable filter (AOTF) 60 with optical polarizer 62 receives the return radiation from the imaging lenses 58. The unrefracted beam 64 emerging from the AOTF 60 strikes a beam blocker 65 while the refracted beam 66 from the AOTF 60 is received by a two-dimensional image detector 68, such as a charge coupled device (CCD) imager. The image detector 68 is controlled by a driver 70 which supplies the image data to a personal computer 72 that collects, processes and displays the image data. The personal computer 72 also drives the power supply 67 of acousto-optic tunable filter 60. In the spectral imaging of FIG. 3, a spectrum of every pixel in an image can be recorded. The acousto-optic tunable filter based system using a coherent optical fiber bundle probe allows SERS biomedical imaging.

An alternative detection technique uses the method of Fourier transform Raman to improve the sensitivity of the detection, especially in the near-infrared (NIR) or infrared (IR) range where the optical detection sensitivity in detector noise limited.

SERMED Probes

Figures 4A, 4B, 4C:
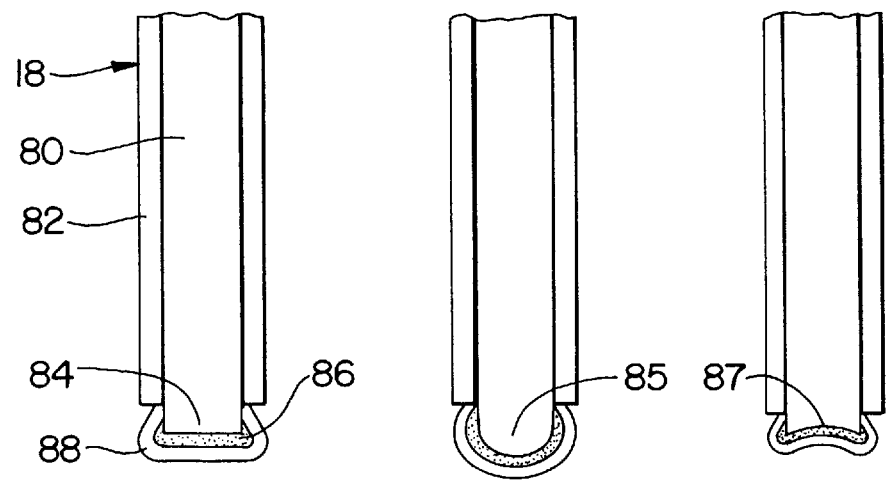
FIGS. 4A–4D illustrate various versions of a first embodiment of a probe for the SERMED apparatus.

With reference to FIGS. 4A–4C, a preferred embodiment of the in vivo probe 18 includes a section of an 600 $\mu$m diameter silica optical fiber 80 with the plastic jacket and cladding 82 removed at one end 84, exposing a 1.0 cm section of bare silica fiber. The probe in FIG. 4B has exposed end forms a concave lens tip 85 and the probe in Figure C has a convex lens tip 87. The bare silica end 84 is cleaned and rinsed using dilute nitric acid, water and ethanol and then polished using alumina polishing sheets (0.5-$\mu$m grain). The tip is then dipped into a five percent aqueous suspension of microparticles 86 (e.g., alumina particles from Baikowski International) for a few seconds. Alumina appears to be one of the most efficient materials for the production of SERS-active substrates. One important advantage of alumina over Teflon (trademark E. I. du Pont de Nemours and Company) or latex microspheres is its relative low cost. This important feature has made alumina a promising material for SERS-active substrate development and most suitable for practical applications. The reproducibility of alumina-based SERS substrates is excellent; the relative standard deviation was found to be less than five percent.

The fiber tip is allowed to dry and then is placed in a vacuum evaporation system where a silver coating 88 is applied. The rate of silver deposition is approximately 0.15 nm/sec at $2\times10^{-6}$ Torr to produce a silver coating having a thickness of 100 nm.

Figure 4D:
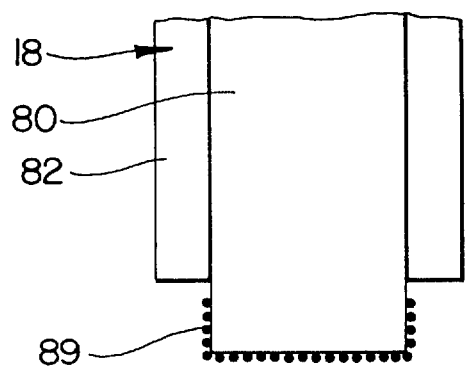

In another embodiment of a probe shown in FIG. 4D, the alumina dipping procedure is not required. In this case, the silver coating 89 has a thickness of 100 nm or less, such that the silver film consists of small islands.

In any of the versions of the probe 18 shown in FIGS. 4A–4D, the silver coating may replaced by another metal capable of inducing the SERS effect. Examples of such metals are gold, nickel, copper and cadmium.

In another embodiment shown in FIG. 5, comprises a probe 18 with a tapered tip 90. The tapered tip 90 is prepared, and drawn from a 60-$\mu$m diameter silica optical fiber 92 down to a desired diameter (e.g., 1.0 $\mu$m or less) using a fiber drawing device, such as one available from Sutter Industries. A layer 94 of microparticles, such as alumina, is applied to the fiber tip 90 before the tip is coated with a silver layer 96. The tapered tip 90 allows measurements for small samples and provide alternative excitation/emission geometry.

A further embodiment of a SERMED probe includes a tip sleeve designed to be disposable in order to avoid cross contamination. With reference to FIGS. 6A and 6B the exposed end 100 of the optical fiber 102 may be cut straight across, concave or tapered. The exposed end 100 then is inserted into a removable cup-like tip sleeve 104 of a light transmissive material, such as a plastic or a polymer. The tip sleeve 104 has an outer surface with microparticle and metal layers 106 and 108 applied thereto. As an option, a liquid 109 with matching index of refraction can be used at the connector to minimize transmission loss from the fiber 18 to the disposable tip sleeve 104.

As depicted in FIG. 7 the SERMED probe 18 can be formed by a disposable tip cap 110 to avoid cross contamination. The tip cap 110 comprises a tip 112 of optical fiber material with an end that has the desired shape, a tapered tip is illustrated. The end of the tip 112 is coated with layers 114 of microparticles and silver. A removable tubular coupling 116 attaches the tip 112 to the exposed end of the optical fiber 30. An optional liquid 118 with matching index of refraction may be applied between the tip 112 and the optical fiber 30.

With reference to FIG. 8, the SERMED probe 18 is coated by with a polymer coating 120 that concentrate specific compounds of interest onto the probe for improved sensitivity. In this version, microparticle and silver layers 121 and 122 are applied to the exposed end of the optical fiber 30. The polymer coatings 120 is applied over these layers 121 and 122.

Figure 9:
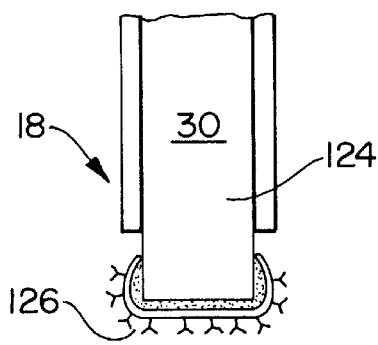
FIG. 9 illustrates a sixth embodiment of a probe for the SERMED apparatus.

As shown in FIG. 9 yet another probe embodiment 124 has a coating of a bioreceptor, such as an antibody of a compound of interest, a protein, an enzyme, a nucleic acid, a cell, a synthetic biological entities, or a molecular imprint material designed to concentrate specific compounds of interest onto the probe for improved sensitivity. Molecular imprint materials are well known and comprise a synthetic material designed with specific geometric contours in order to recognize chemical or biological species. In this embodiment, the microparticle and silver layers are covered by the bioreceptor coating 126.

Figure 10A:
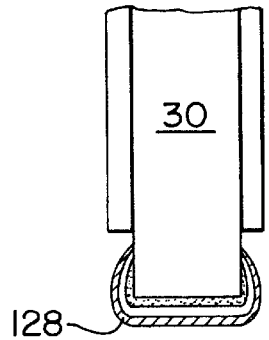
FIGS. 10A, 10B and 10C illustrate other embodiments of a probe for the SERMED apparatus.

Alternatively where any of the previously described SERMED probes has to be in contact with or close to the tissue or samples to be examined may have a protective and biocompatible coating 128 as seen in FIG. 10A.

Figure 10B:
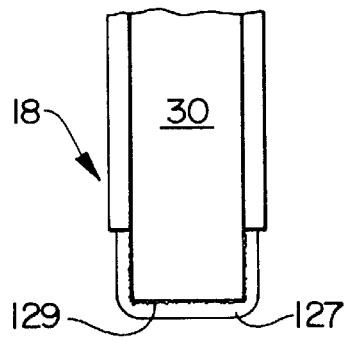

Alternatively where any of the previously described SERMED probes employ a microparticle layer, the surface of the probe 30 can be fabricated with a microstructured surface 129 using preformed molding fabrication or a layer of coating of optically transmissive material. In this case shown in FIG. 10B, the microstructured surface has protrusions projecting therefrom for a distance between one nanometer and one micrometer. A metal coating 127 is evaporated directly onto the microstructured surface without requiring nanoparticles of alumina.

Figure 10C:
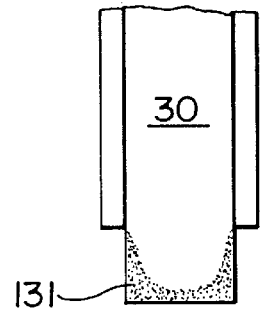

In another embodiment shown in FIG. 10C, the SERMED probe 30 comprises material, such as a polymer, plastic or gel, with embedded nano particles of metal 131 as indicated by the stippling.

Figure 11:
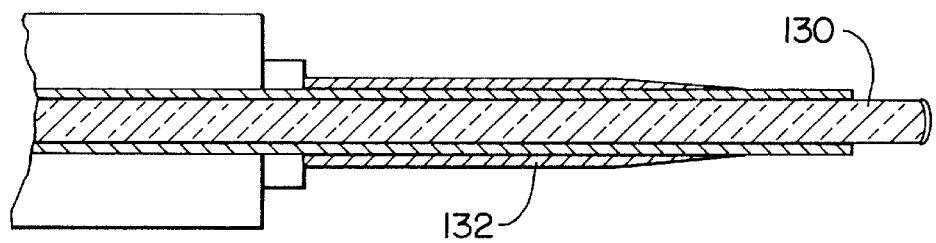
FIG. 11 illustrates an embodiment of a SERMED probe inserted in a needle for delivery an organ being examined.

Referring to FIG. 11, for applications in which the probe is to be delivered onto internal organs, a SERMED probe 130 can be inserted into a needle 132 or through a channel of an endoscope.

Figure 12:
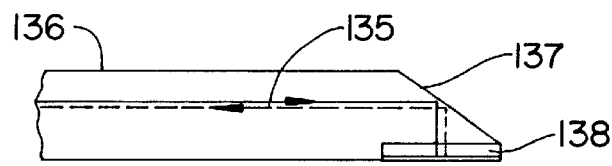
FIG. 12 illustrates an embodiment of a SERMED probe with side excitation and emission.

FIG. 12 illustrates a SERMED probe 136 with the exposed end 137 cut at a 45 degree angle and having a reflective coating applied thereto. The laser beam 135 is reflected by the exposed end 137 through a side of the SERMED probe 136 and through a region 138 on which microparticle and metal layers are applied.

SERMED Measurements

In order to demonstrate the proof of principle of the SERMED approach, various probes described above were used to perform measurements on a variety of samples, tissues and tumors using homogenized samples as well as intact in vitro samples. In vivo measurements also were performed on skin samples.

a) In Vitro Measurements

FIG. 13A shows the SERS spectrum of a homogenized sample (approximately 1 g in PBS-phosphate buffer saline solution) from rat heart tissue sample using the SERMED method. The SERMED probe was coated with alumina and 100-nm layer of silver. The excitation was at 514.5 nm (argon ion laser, 25 mW). The results show several SERS spectral structures at about 1000 cm$^{-1}$. On the other hand, the Normal Raman Scattering (NRS) spectrum of the rat heart tissue, shown in FIG. 13B, does not exhibit any spectral structure, only a broad background due to fluorescence emission. These results demonstrate the two important advantages of the SERMED approach as compared to the NRS method: (a) subtle spectral structures are detected using SERMED, and (b) the strong fluorescence background is decreased.

Figure 14A:
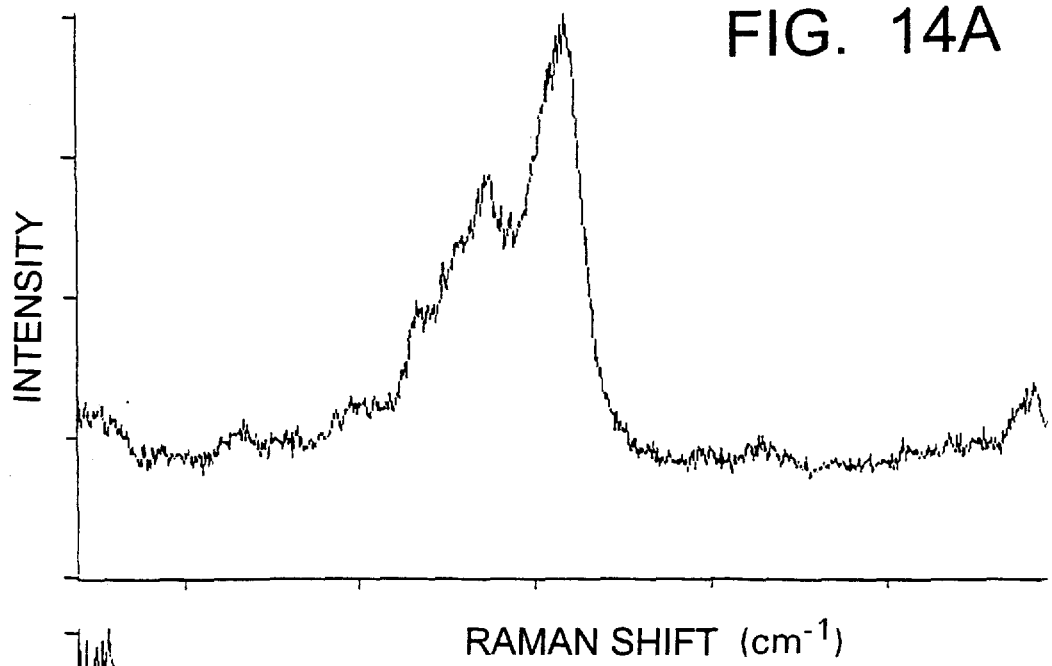
FIGS. 14A and 14B show the SERS spectrum and NRS spectrum respectively of a homogenized sample of rat stomach tissue.
Figure 14B:
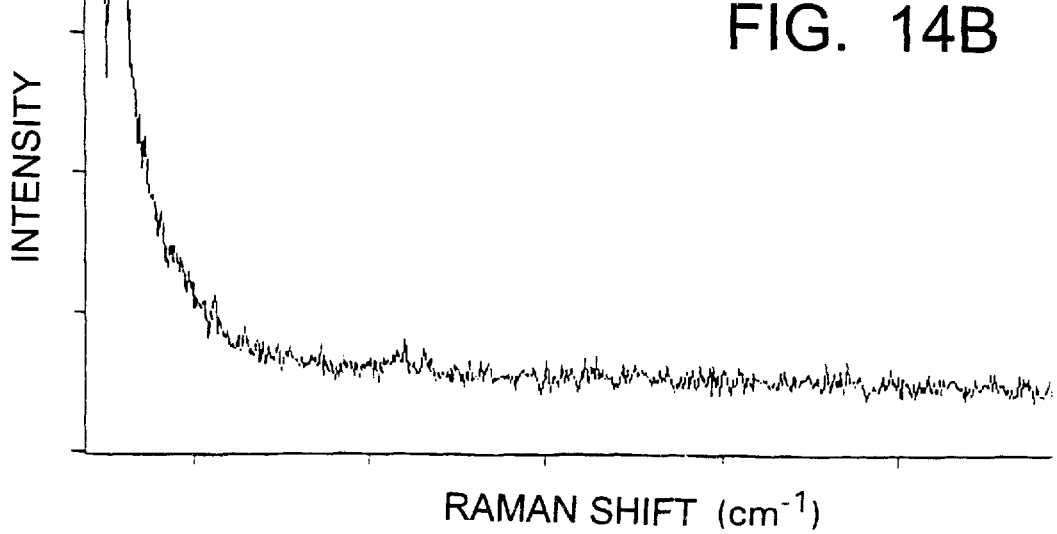

FIG. 14A shows the SERS spectrum of rat stomach tissue (homogenized) using 514.5 nm laser excitation under conditions described above. Comparison with the NRS spectrum (FIG. 14B) of the same rat stomach sample also indicates that the SERS method is more sensitive and provide more spectral structures (e.g., peak 2900 cm$^{-1}$). It is noteworthy that the SERS spectra of rat heart and stomach tissues (FIGS. 13A and 14A) are similar, but not exactly the same. This indicates the possibility of identifying the type of tissue using the SERMED method.

Figure 15A:
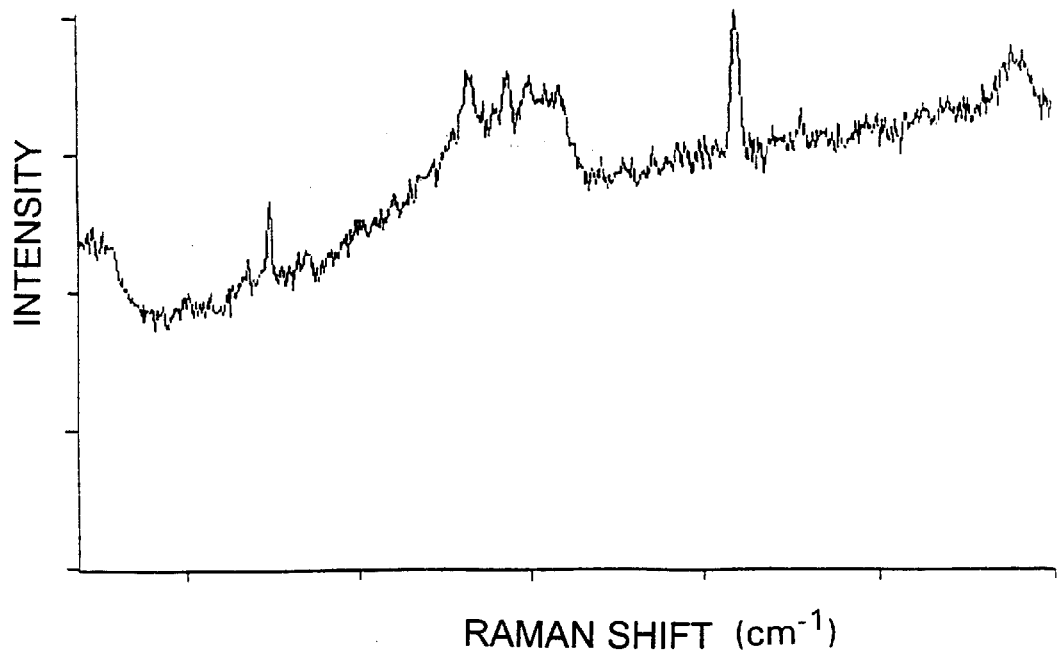
FIGS. 15A and 15B show the SERS spectrum and NRS spectrum respectively of a homogenized sample of rat kidney tissue.
Figure 15B:
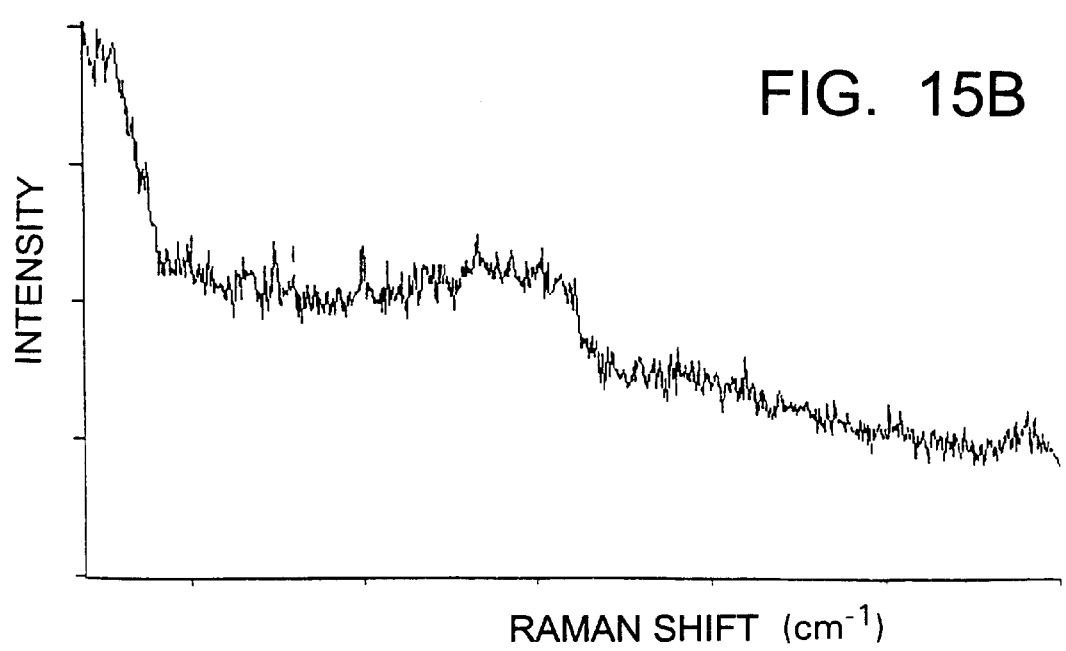

The SERS spectra of homogenized sample of rat kidney samples using two different laser excitation. The results produced by an argon ion laser at 514.5 nm, 25 mW are shown in FIG. 15A, while the results from a krypton ion laser at 647.1 nm, 25 mW are shown in FIG. 15B. Several sharp SERS peaks are identified in both spectra.

Figure 16A:
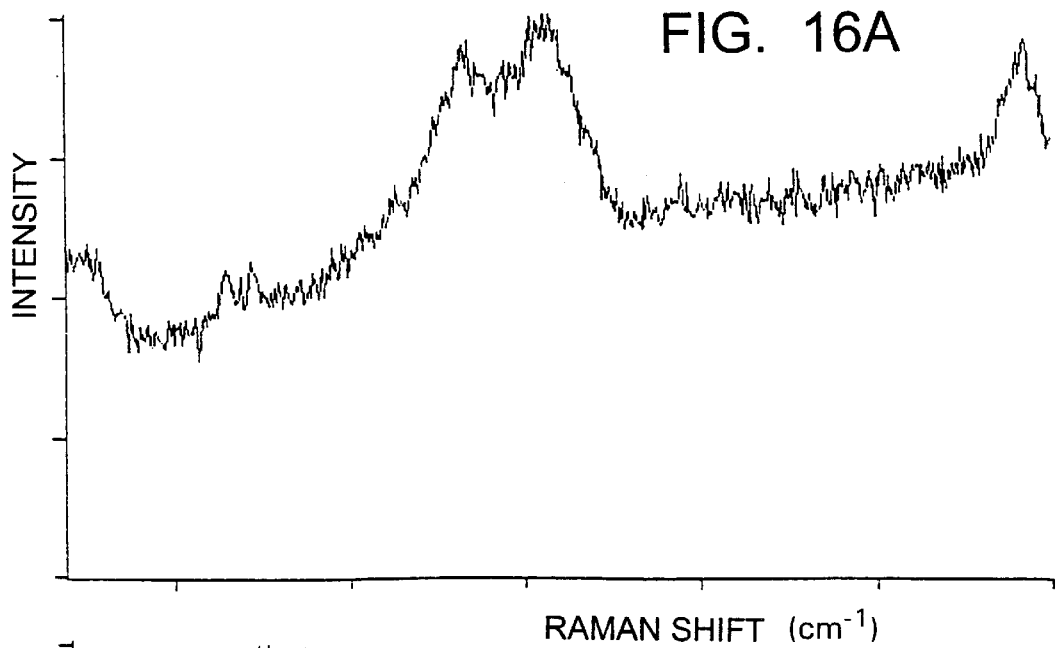
FIGS. 16A and 16B show SERS spectra of rat tumor samples respectively using argon ion laser excitation and krypton ion laser excitation.
Figure 16B:
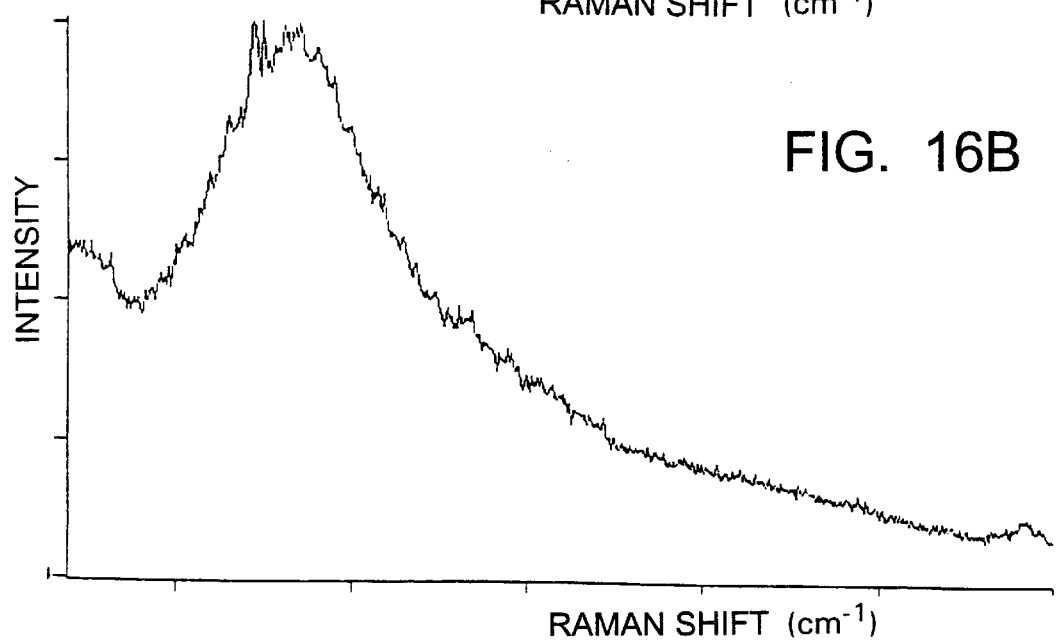

FIGS. 16A and 16B respectively show SERS spectra of rat tumor samples (Tumor TX1) using argon ion laser excitation at 514.5 nm, 25 mW and krypton ion laser excitation at 647.1 nm, 25 mW. Several SERS peaks are identified in both spectra, which are different from normal tissue samples.

b) SERMED Measurements for Biomedical Screening

Figure 21:
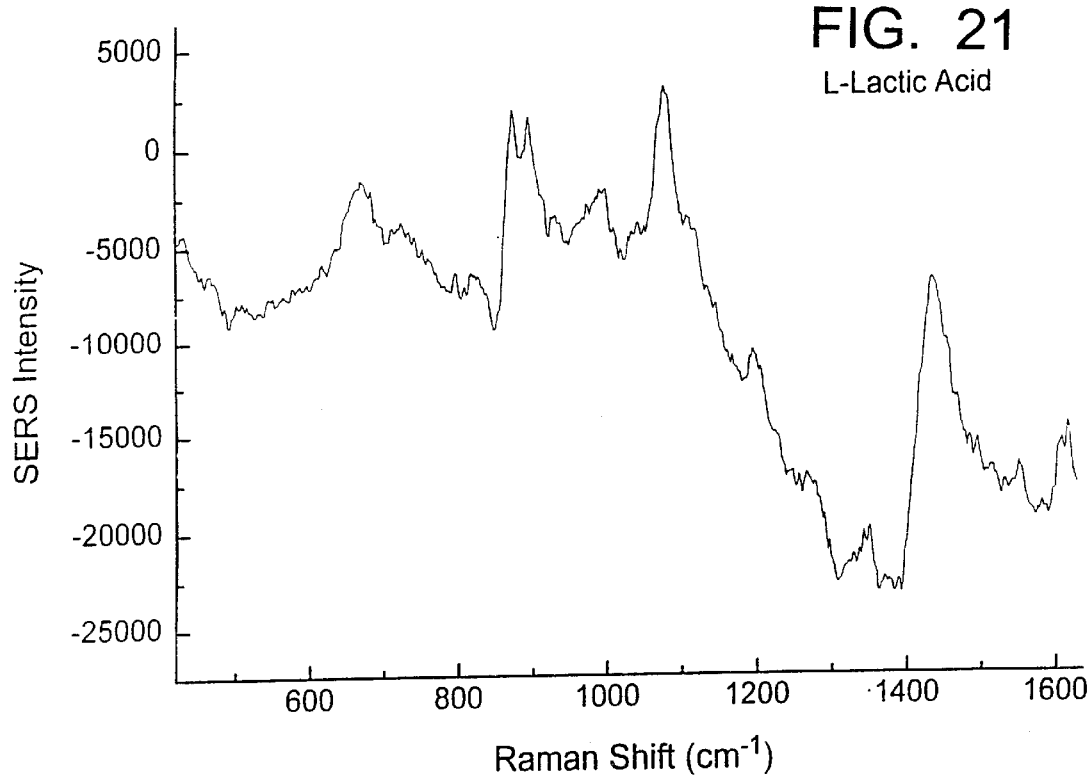
FIG. 21 illustrates SERMED analysis to identify and quantify lactic acid.
Figure 22:
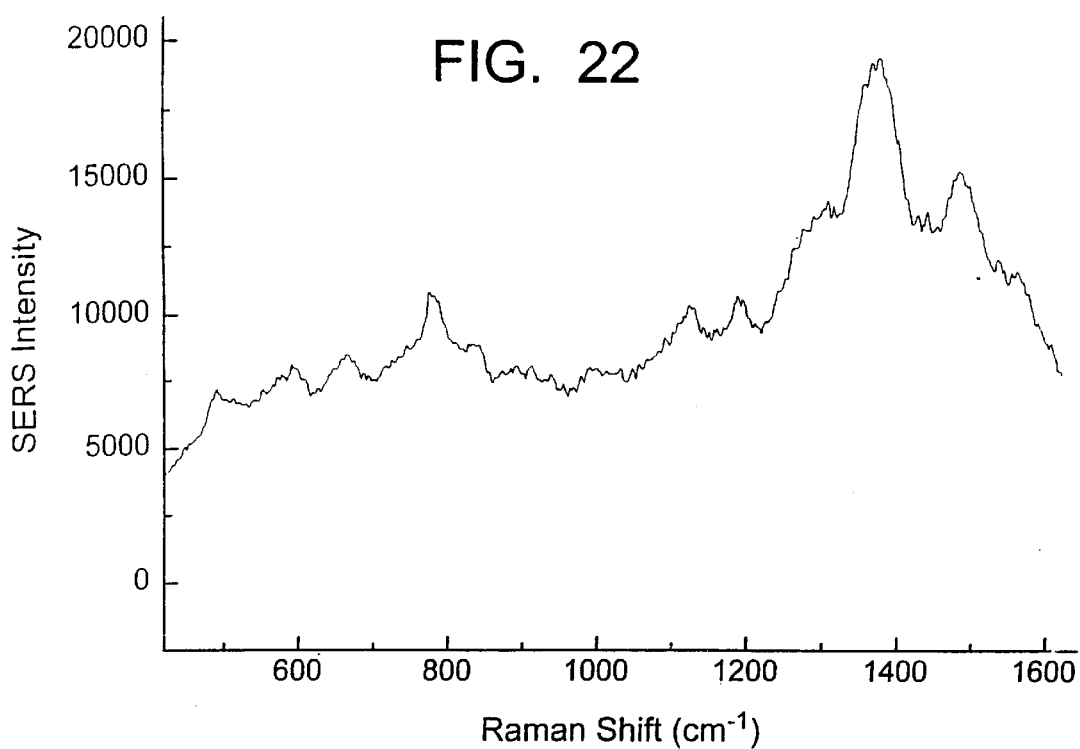
FIG. 22 depicts SERMED analysis results that identify and quantify FAD.

Knowledge of the presence and concentration of various biochemical compositions in the body or in bodily fluids (blood, urine, sweat, etc.) could provide information on the health of a person. These experimental results indicate the possibility of SERMED to identify and quantify important biochemical species for biomedical screening. FIG. 17 illustrates the results of SERMED analysis to identify and quantify cholesterol. FIG. 19 demonstrates SERMED analysis to identify and quantify glucose for diagnosis and treatment of diabetes, and FIG. 19 shows results of SERMED analysis to quantify insulin for monitoring diabetics. FIG. 21 illustrates SERMED analysis to identify and quantify lactic acid in injured patients. The results of SERMED analysis to identify and quantify NADH are graphically depicted in FIG. 20 and FIG. 22 depicts SERMED analysis results that identify and quantify FAD. The SERMED instrument also can be employed to monitor hematoporphyrin in PDT patients, quantify 1-Hydroxypyrene for occupational exposure to PAH, and to analyze urine. Measurements of these and other relevant compounds can be performed in vitro and in vivo using the appropriate SERMED techniques and probes.

c) In Vivo Measurements for Diagnosis

Figure 23:
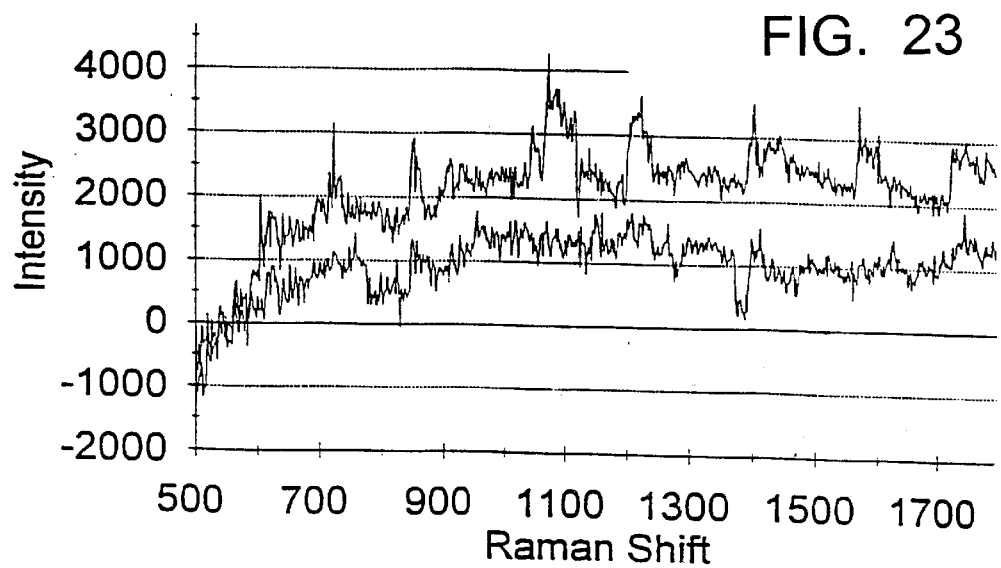
FIG. 23 demonstrates the use of a SERMED system for in vivo analysis of skin tissues.

One main advantage of the proposed SERMED probes is the capability of making in vivo measurements in a non-invasive manner (i.e. tissue is not required to be removed). In this application, the SERMED probe is used to enhance the Raman signal from the samples that are in contact with the probe. In some case a liquid may be applied between the probe and the in vivo sample. To demonstrate this possibility, SERS measurements were preformed on skin tissues of two individuals. The spectra in FIG. 23 show several SERS peaks. The results indicate that it is possible to use the SERMED system for in vivo analysis of tissues. Although the proof of concept measurements were performed on skin, the method is generally applicable to any organ accessible by the probes: gastro-intestinal tract, heart, lung, cervix, breast, etc. The SERMED probes can be inserted into an endoscope (e.g., GI tract, colonoscopy) or a needle (breast, heart diagnosis), or used with a disposable tip or sleeve (cervix diagnosis).

d) Use of SERMED for Non-Invasive Drug Screening

Individuals who use drugs may have trace compounds of these drugs remaining on their fingertips, as in the case of tobacco users. Another possibility is the natural secretion of these drugs or related metabolites through sweat and urine, or other bodily fluid. It is possible to use the SERMED device to detect these substances directly on the skin surface or directly on the sweat/oils secreted on the skin.

Figure 26:
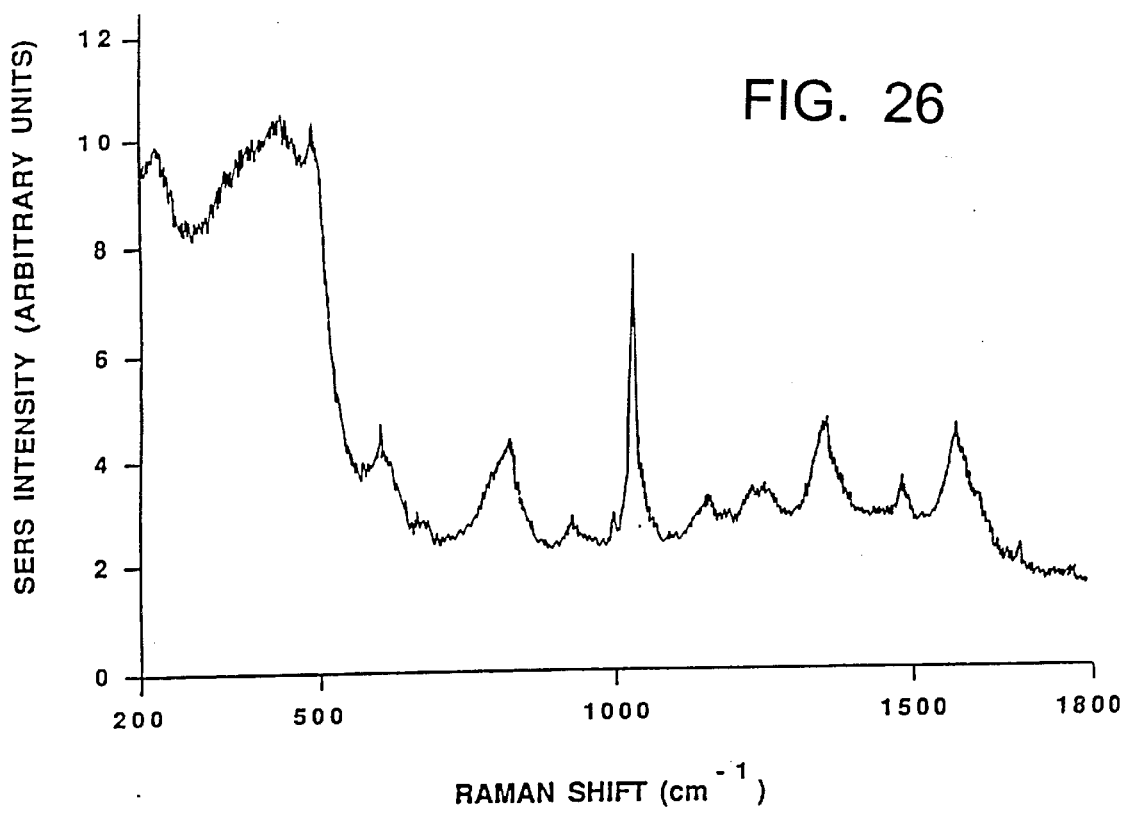
FIG. 26 shows the SERS peak characteristic of nicotine.

To demonstrate this possibility we have performed in vivo measurements by placing SERMED probes on finger tips of various individuals. The results indicate that SERS spectra of finger tips of tobacco users (smokers) show a characteristic peak at approximately 1005 cm$^{-1}$ in FIG. 24, which is absent in non-smokers in FIG. 25. Note that the peak at approximately 1030 cm$^{-1}$ is similar to the SERS peak characteristic of nicotine seen in FIG. 26. This screening approach may me used to screening for other types of substances such as cocaine.

Figure 24:
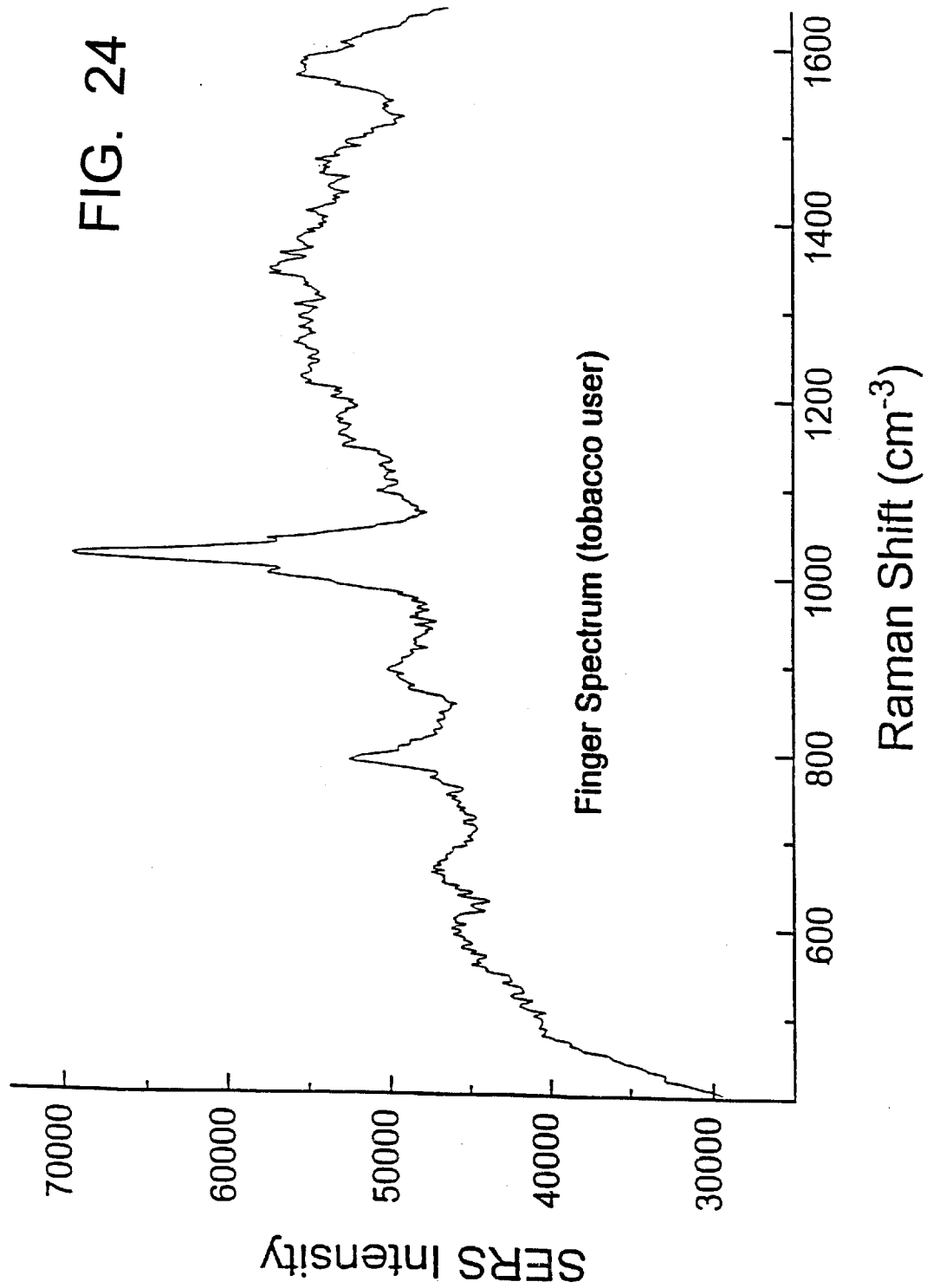
FIG. 24 illustrates the SERS spectra of finger tips of tobacco users.
Figure 25:
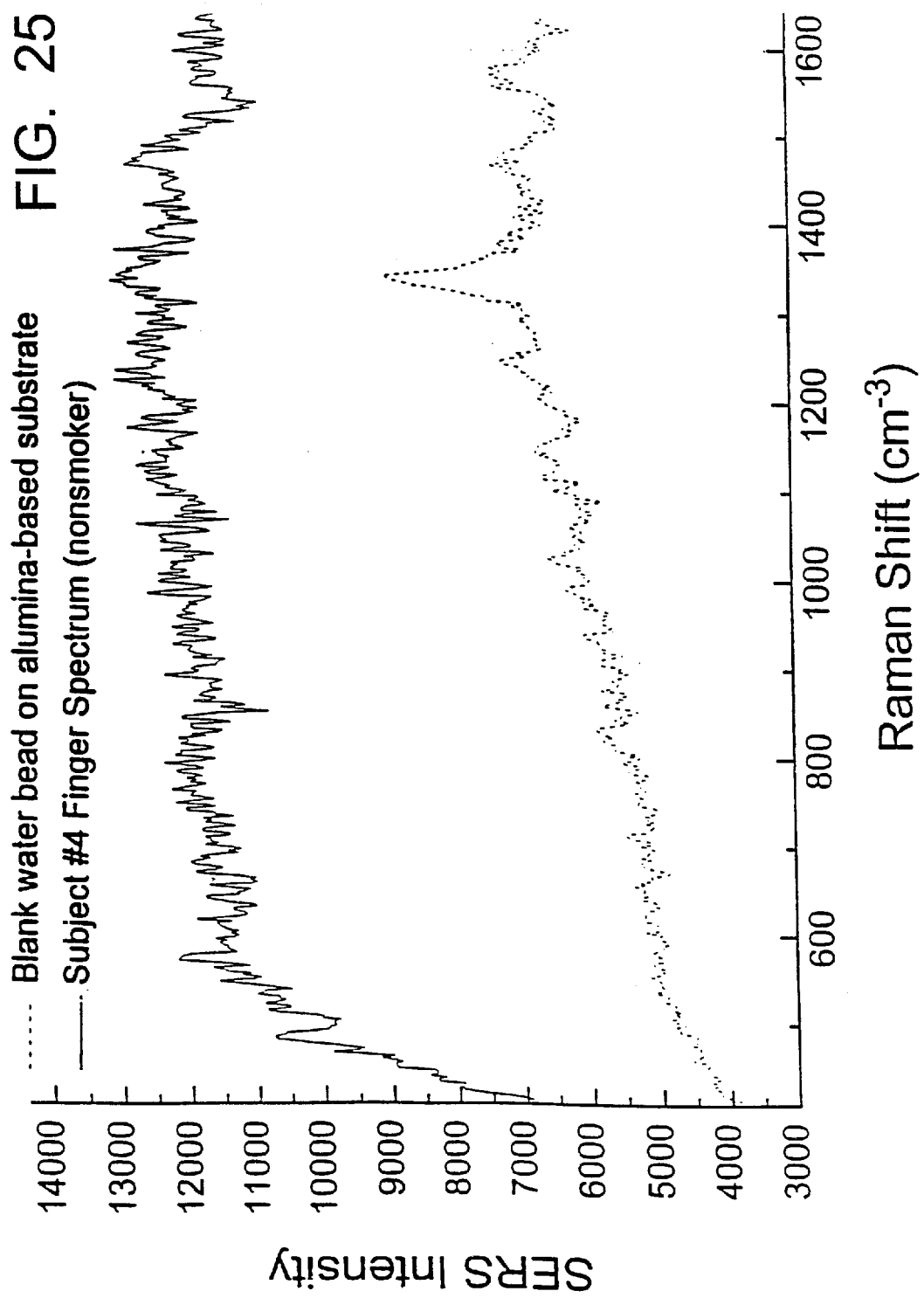
FIG. 25 illustrates the of SERS spectra of finger tips of non-tobacco users.

The results in FIGS. 24 and 25 are significant because they demonstrate the operative principle of the SERMED probe for non-invasive in vivo analysis. These results indicate that the SERMED probe, when placed in contact with a tissue sample, can produce an enhancement of the Raman signal of compounds in that tissue sample. The SERMED technique and probes allow rapid in vivo and in situ analysis and can be used for non-invasive biomedical diagnosis at clinical offices and rapid drug testing in the workplace.

I claim:

1. A probe for a surface-enhanced Raman scattering spectrometer which has a source of excitation radiation and a detector for radiation emitted from a specimen being examined, the probe comprising:

a member of optically transmissive material for receiving the excitation radiation from the source and for carrying the radiation emitted from the specimen to the detector, the member having an end for placing against to the specimen;

a layer of optically transmissive material coated on the end of the member with the coating having a microstructured surface with protrusions; and metal material applied to the layer of optically transmissive material for producing surface enhancement of the specimen during Raman scattering spectroscopic analysis.

2. The probe as recited in claim 1 wherein the member comprises an optical fiber.

3. The probe as recited in claim 1 wherein the end of the member is shaped to form a lens system.

4. The probe as recited in claim 1 wherein the end of the member is tapered.

5. The probe as recited in claim 1 wherein the metal material comprises metal particles between a one nanometer and one micrometer in size.

6. The probe as recited in claim 1 wherein the protrusions are between one nanometer and one micrometer high.

7. The probe as recited in claim 6 wherein the optically transmissive material is a polymer.

8. The probe as recited in claim 6 wherein the metal material comprises a layer of metal applied over the coating of optically transmissive material.

9. The probe as recited in claim 6 wherein the metal material comprises metal particles embedded the layer of optically transmissive material.

10. The probe as recited in claim 9 wherein the metal material is selected from the group consisting of alumina and titania.

11. The probe as recited in claim 1 wherein the metal material comprises a layer of a metal having a thickness of substantially no greater than 100 nm, thereby producing islands of metal at the end of the member of optically transmissive material.

12. The probe as recited in claim 11 wherein the layer of metal is selected from the group consisting of silver, gold, nickel, copper and cadmium.

13. The probe as recited in claim 1 further comprising a bioreceptor layer applied to the end of the member to concentrate onto the probe compounds to be analyzed spectroscopically.

14. The probe as recited in claim 1 further comprising a layer of a material applied to the end of the member to concentrates onto the probe compounds to be analyzed spectroscopically.

15. The probe as recited in claim 14 wherein the a layer of a material is selected from the group consisting of a polymer, an antibody, a protein, an enzyme, a nucleic acid and a molecular imprint material.

16. The probe as recited in claim 1 further comprising a sleeve of a material that is transparent to the excitation radiation wherein the sleeve removably extends around the end of the member, and the metal material is applied to the sleeve.

17. The probe as recited in claim 1 further comprising a removably coupling for attaching the member to an optical fiber.

18. The probe as recited in claim 1 wherein the member has an end surface that is beveled with a reflective material applied thereto, and the coating is applied to a side surface of the member through which the excitation radiation is reflected by the reflective material.

* * * * *